United States Patent [19]
Usui et al.

[11] Patent Number: 5,655,904
[45] Date of Patent: Aug. 12, 1997

[54] DENTAL MIRROR

[75] Inventors: Masayoshi Usui, Numazu, Japan; Yoshiki Oshida, DeWitt, N.Y.

[73] Assignee: Usui Kokusai Sangyo Kaisha Ltd., Japan

[21] Appl. No.: 581,154

[22] Filed: Dec. 29, 1995

[51] Int. Cl.$^6$ ................................................. A61B 1/24
[52] U.S. Cl. ................................................................ 433/30
[58] Field of Search ........................ 433/30, 31; 600/248, 600/249; 359/838, 882, 886

[56] References Cited

U.S. PATENT DOCUMENTS

| | | | |
|---|---|---|---|
| 1,065,110 | 6/1913 | Bustanoby | 359/882 X |
| 1,843,067 | 1/1932 | De Terra | 433/30 X |
| 2,275,201 | 3/1942 | Reily | 359/882 |
| 3,859,987 | 1/1975 | Holstad | 433/30 X |

FOREIGN PATENT DOCUMENTS 992475  10/1951  France ...................... 433/51

Primary Examiner—Nicholas D. Lucchesi
Attorney, Agent, or Firm—Anthony J. Casella; Gerald E. Hespos

[57] ABSTRACT

The present invention provides a sanitary dental mirror for diagnosing and observing a diseased part of a mouth which can prevent an undesired foggy mirror surface. A dental mirror used for diagnosing and observing a diseased part of a patient's mouth is provided with a stem portion, a distal end portion, a mirror attached on one surface of the distal end portion, and a holding member having a concave-shaped filling canister. The dental mirror furthermore comprises a certain type of substance which is filled in the concave-shaped filling canister and stores heat generated by an absorbing reaction with moisture, a lid which has a plurality of small through-holes and opens/closes an opening portion of the concave-shaped filling canister, and a sealing film which is temporarily adhered on the outer surface of the lid.

10 Claims, 4 Drawing Sheets

DENTAL MIRROR

BACKGROUND OF THE INVENTION

1. Field of the Invention

The present invention relates to a dental mirror which prevents foggy surface conditions caused by intraoral moisture and temperature during dental diagnosing and treatment.

2. Description of the Prior Arts

A dental mirror is routinely utilized as a tool to observe intraoral conditions, particularly on lingual sides of the teeth. The dental mirror normally is made of metallic material and is supplied as a unitary structure that is sterilizable with chemical or thermal treatments. Recently, due to intra-hospital infections and/or contagions, including AIDS, the whole structure of the dental mirror is fabricated from plastic and is discarded after a single use.

However, when any type of a dental mirror is used inside the patient's mouth, the surface of said dental mirror becomes foggy due to humidity and temperature largely entrapped in exhaled air during respiration. Such foggy-surface conditions might cause errors in diagnoses and treatments. Once a dentist or dental assistant recognizes the surface of the mirror to be foggy, the mirror is removed from the patient's mouth and the mirror surface is blown to clear the foggy surface, or, if necessary, a new dental mirror is utilized.

Under the aforementioned situations associated with foggy surfaces of conventional dental mirrors, chair-side time (or dental treatment time) could be prolonged, or an additional procedure such as sterilization may be required.

SUMMARY OF THE INVENTION

All of the foregoing has resulted in a need for a sanitary dental mirror which prevents a foggy surface when said dental mirror is used in a humid intraoral environment.

After extensive research and development efforts, the present inventors have reached the following invention which achieves the aforementioned object.

According to the first embodiment of the present invention, a dental mirror used for observing and diagnosing the affected area inside a patient's mouth comprises a stem portion and a distal end portion. One side of the distal end portion is covered with a mirror, and the other side thereof is formed with a holding member which has a concave-shaped filling canister. The concave-shaped filling canister is filled with a substance which is able to store heat generated by an absorbing reaction with the moisture of a patient's mouth. An opening portion of the concave-shaped filling canister is furthermore closed with a lid in which a plurality of through-holes, each having a small diameter, are formed. Moreover, the outer surface of the lid is covered temporarily with a sealing film.

According to the second embodiment of the present invention, a dental mirror employed for diagnosing and observing the diseased part inside of a patient's mouth consists of a stem portion and a distal end portion. The distal end portion is formed with a holding member. One side of the holding member is covered with a mirror. On the rear side of said mirror, a receptacle is adhered which is filled with a certain type of substance to store heat generated by an absorbing reaction with the moisture of a patient's mouth. A plurality of small size through-holes are formed on one side of the receptacle. Furthermore, a sealing film is temporarily adhered on the outer surface of said receptacle.

The stem portion and the distal end portion can be formed either as a unitary structure, or structured in such a way that both portions can be easily assembled and/or disassembled. Substances for storing heat which is generated by an absorbing reaction with the humidity of a patient's mouth can be zeolite, quick lime (calcium oxide), silica gel (gel of silicon dioxide), active alumina (aluminum oxide), plaster of Paris (calcium sulfate), or the like. Furthermore, the lid can be designed and manufactured in such a manner that it can be easily assembled and/or disassembled, or opened and/or closed.

BRIEF DESCRIPTION OF THE DRAWINGS

The above objectives, features and advantages of this invention will be more fully understood from the ensuing detailed description of the preferred embodiments of the present invention, which description should be read in conjunction with the accompanying drawings wherein.

DETAILED DESCRIPTION OF PREFERRED EMBODIMENTS

Figure 1:
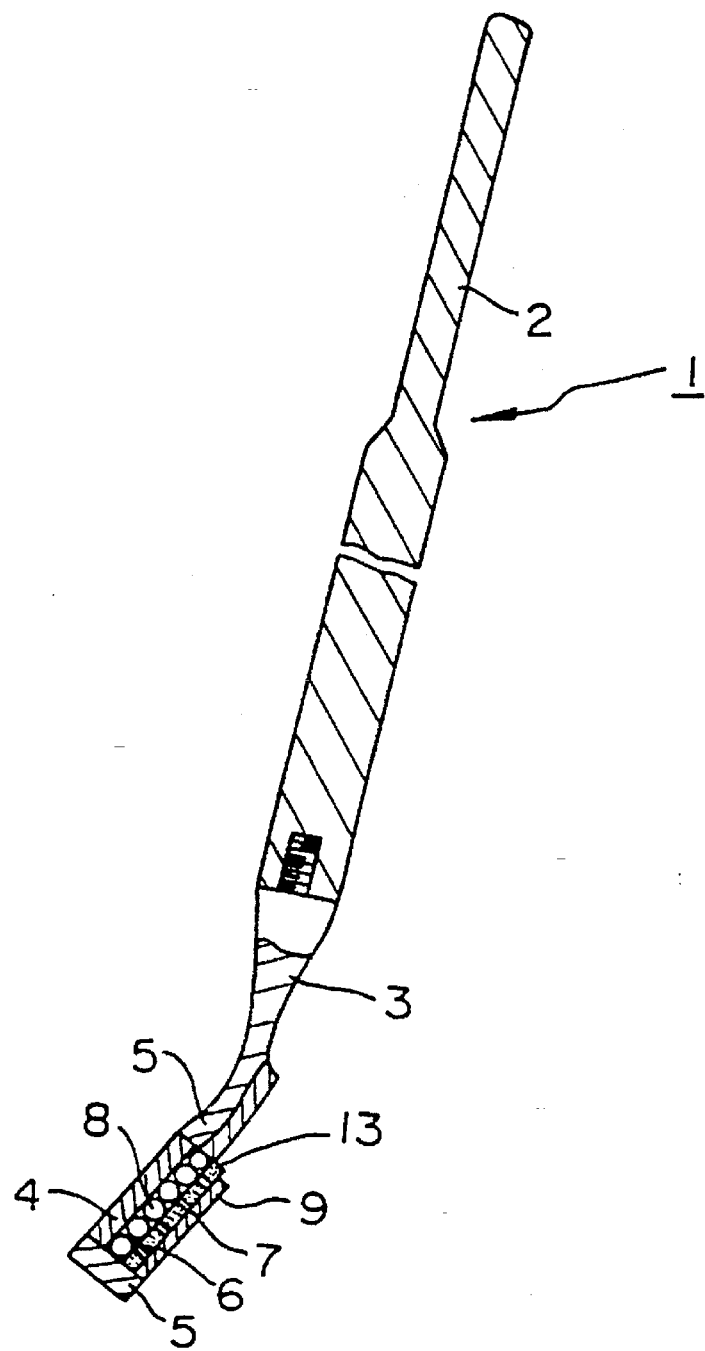
FIG. 1 is a cross sectional view of an embodiment according to the present invention.
Figure 2:
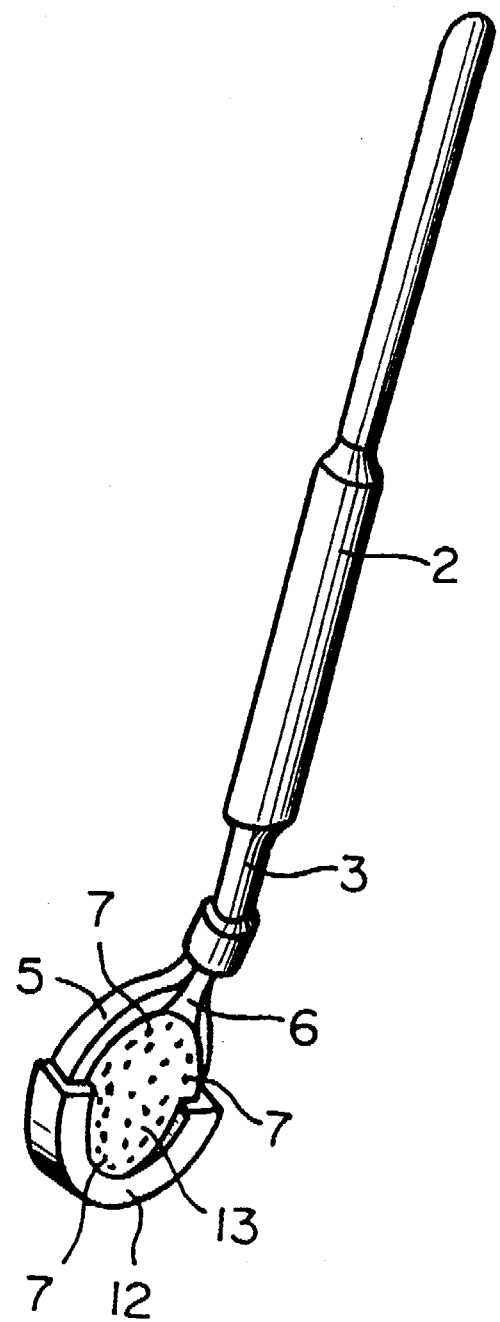
FIG. 2 is a perspective view of an embodiment shown in FIG. 1 according to the present invention.
Figure 3:
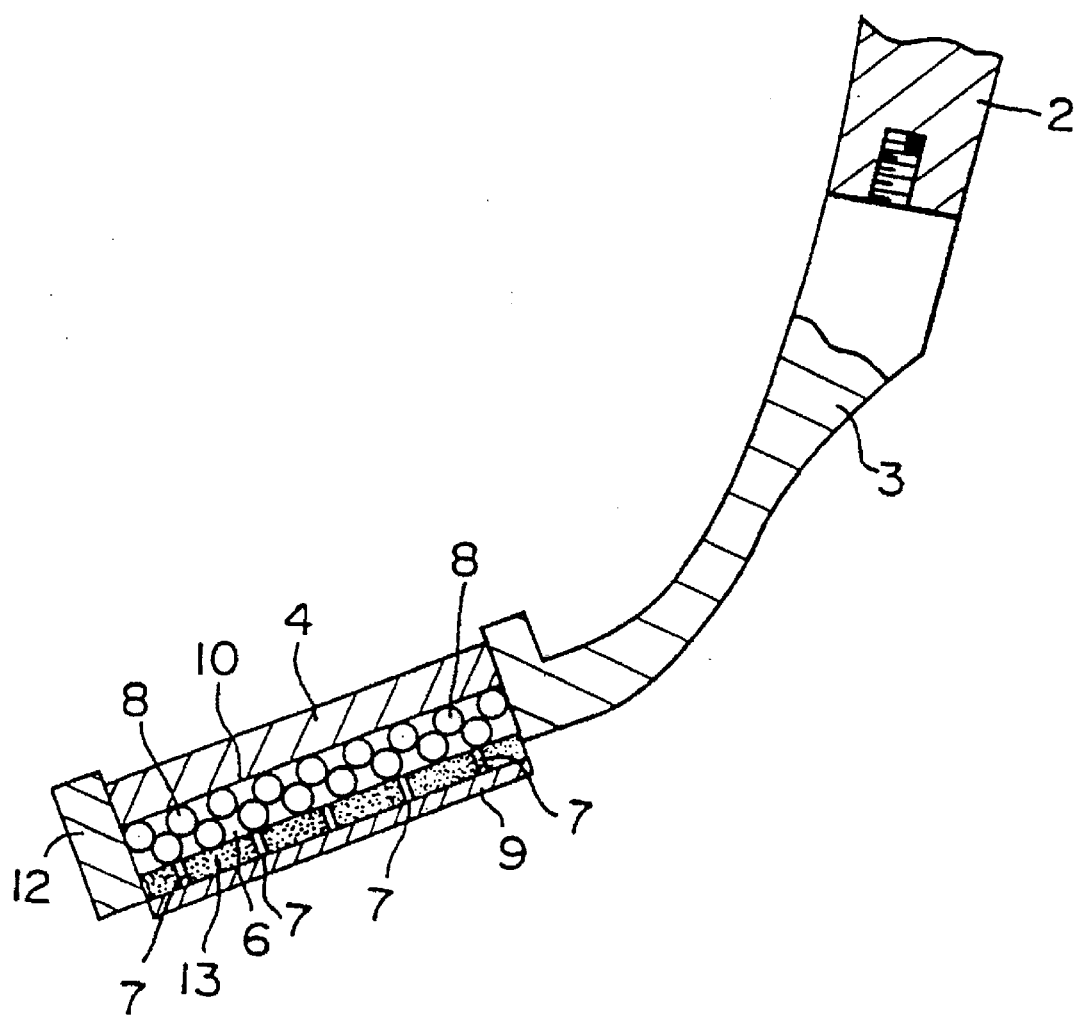
FIG. 3 is a side cross sectional view of another embodiment of the present invention.

Referring to the attached drawings, as seen in FIGS. 1 through 3, the dental mirror 1, used for diagnosing and observing a diseased area inside a patient's mouth, comprises a stem portion 2 and a distal end portion 3. The distal end portion 3 furthermore consists of a mirror 4, a holding member 5, and a concave-shaped filling canister 6. The mirror 4 is attached to a first surface of said holding member 5. Moreover, the concave-shaped filling canister 6 is provided on a second surface which opposes the rear side of the mirror 4. A lid 13 having a plurality of small size through-holes 7 is provided at an open portion of said concave-shaped filling canister 6. A substance which can store heat generated by an absorbing reaction with the moisture of a patient's mouth is filled inside the concave-shaped canister 6.

A sealing film 9 is temporarily adhered to the outer surface of the lid 13 in which a plurality of small size through-holes 7 are formed. Prior to the use of the dental mirror in the mouth, the sealing film 9 is detached from the outer surface of the lid 13.

Moreover, the stem portion 2 and the distal end portion 3 both of which form the dental mirror 1 can be unitarily structured and made from plastic material or stainless steel. Alternatively, the stem portion 2 can be made from stainless steel and the distal end portion 3 may be fabricated from plastic material. Furthermore, the stem portion 2 and the distal end portion 3 can be screwed together so that they can be easily assembled and/or disassembled. On the other hand, in a case when quick lime (calcium oxide) is used as the substance 8, only the distal end portion 3 can be formed to be disposable, so that intra-hospital infection or contagion caused by the dental mirror can be avoided.

As described previously, since the substances 8 have granular shapes, the foggy surface condition of the dental mirror upon fabricating thereof or using thereof can be effectively avoided. This is mainly due to the fact that the granular particles of the substance 8 possess a large surface area for the effective reaction with the exhaled atmosphere in the patient's mouth, so that the absorbing effect of moisture can be substantially enhanced.

The surface of the absorbing media 8 inside the concave-shaped filling canister 6 directly contacts the rear side surface of the dental mirror 4. Thus the heat of the substance 8, generated by the stored heat due to the absorption of moisture, can be transferred to the mirror 4. This effectively prevents a foggy condition of the mirror surface 4.

The lid 13 for closing the open portion of the concave-shaped filling canister 6 can be formed for easy assembly and/or disassembly, so that only substance 8 disposed inside the concave-shaped filling canister 6 is required to be replaced.

The substance 8 for storing heat generated by the absorbing reaction with the moisture in the intraoral atmosphere can be selected from a group consisting of zeolite, quick lime, silica gel, active alumina, plaster of Paris, or the like. Any other type of material also can be used if it is not biologically toxic and if it can store the heat due to the absorbing reaction with the intraoral moisture.

According to the embodiment described above, the surface of the dental mirror is free from the foggy situation due to a synergistic effect of the storing function of heat by the substance 8 through contacting the moisture of the patient's mouth and through the heating function of the substance 8 associated with the absorbing reaction with the moisture.

Moreover, when zeolite is used as the substance 8 in the present invention, the zeolite can be used repeatedly by reheating thereof. It was found that zeolite reached the satisfactory temperature even after it was reheated several thousands of time.

Furthermore, the substance 8 can be packaged in a tight-closure condition. The package of the substance 8 can be opened and the substance 8 can be filled into the concave-shaped filling canister 6 by opening the lid 13 of the canister 6. With such a structure, undesired absorbing of moisture during storage can be prevented and the handling during usage may be substantially simplified.

Figure 4:
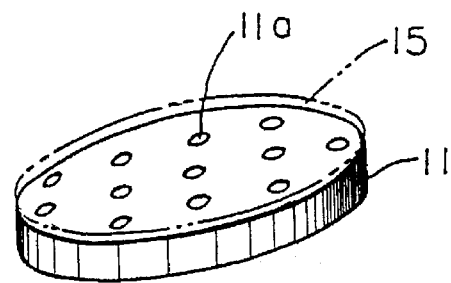
FIG. 4 is a perspective view of a receptacle in which a certain type of substance is filled according to the embodiment of FIG. 3 of the present invention.

Referring to FIG. 4, the second embodiment of the present invention will be explained. As seen in FIG. 4, the substance 8 is filled inside a disk-shaped receptacle 11 on which a plurality of small size through-holes 11a are formed on a first surface thereof. A sealing film 15 is adhered temporarily on the outer surface of said receptacle 11 and a double-side adhesive tape 14 is provided on a second surface of the receptacle 11.

Figure 5:
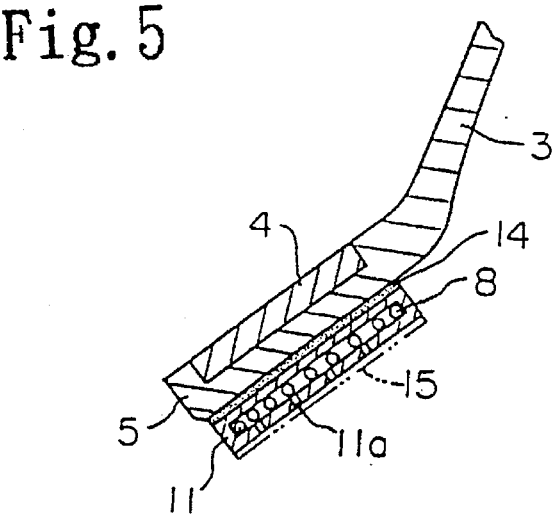
FIG. 5 is a perspective view, demonstrating a case when the embodiment shown in FIG. 4 is applied.

With this structure, as seen in FIG. 5, the receptacle 11 is adhered to the rear surface of the holding member 5 of the distal end portion 3 by using the double-side adhesive tape 14. The moisture inside the mouth can penetrate into the receptacle 11 through small size through-holes 11a after the sealing film 15 is peeled off, so that the moisture reacts with the substance 8 to be heated, resulting in preventing the foggy surface of the dental mirror. The procedure is substantially easy to follow.

Furthermore, the third embodiment of the present invention will be described by referring to FIG. 6, in which the receptacle 11 of FIG. 4 is mounted in the concave-shaped filling portion at the rear side of the mirror 4. A portion of the lid 13 is attached to a part of the stem portion 3 through a hinge or chain mechanism similar to a "locket", so that the lid 13 can be easily opened and/or closed. Although, in this embodiment, the disk-shaped receptacle 11 is utilized, as seen in FIG. 4, the double-side adhesive tape attached to the rear side surface is not required.

Figure 6:
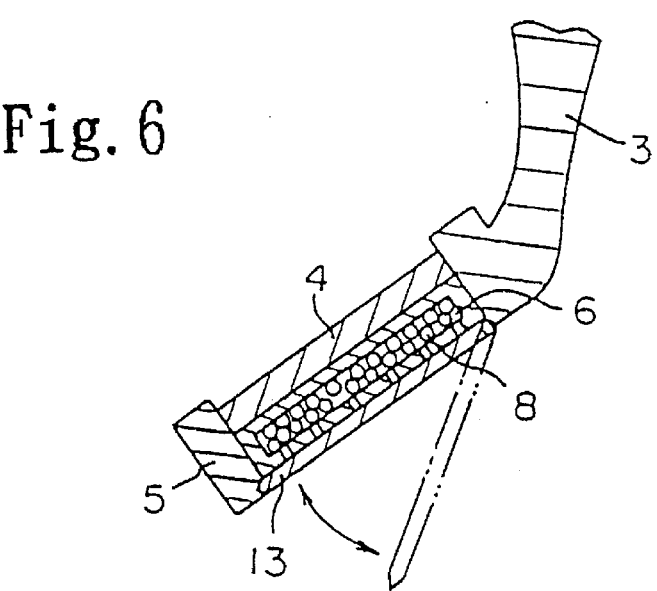
FIG. 6 is a side cross sectional view of a further embodiment according to the present invention.

In the embodiments described in FIGS. 4 through 6, like the embodiment in FIGS. 1 through 3, the stem portion 2 and the distal end portion 3 can be screwed together so as to be detachable, or the canister 1 can be replaceable. Moreover, the entire body of the dental mirror can be made from less expensive plastic material to be disposable. Moreover, zeolite, as a material for the substance 8, can be recycled for re-heating procedures many times.

As has been described above, the present invention can provide a sanitary dental mirror for diagnosing and observing a diseased area of a patient's mouth under fog-free surface conditions.

While the invention has been explained with reference to the structure and function disclosed herein, it is not confined to the details as set forth, and this application is intended to cover modifications and changes as may come within the scope of the following claims.

What is claimed is:

1. A dental mirror for diagnosing and observing a diseased part of a patient's mouth, said dental mirror having a stem portion, a distal end portion, a mirror attached on one surface of said distal end portion, and a holding member having a concave-shaped filling canister; said dental mirror furthermore being provided with a substance which is disposed in the concave-shaped filling canister, said substance being capable of storing heat generated by an absorbing reaction with moisture in the patient's mouth, a lid which has a plurality of small size through-holes and selectively opens and closes an open portion of said concave-shaped filling canister, and a sealing film which is temporarily adhered on an outer surface of said lid.

2. The dental mirror cited in claim 1, wherein said stem portion and the distal end portion are formed as a unitarily structured component.

3. The dental mirror cited in claim 1, wherein the substance capable of storing heat generated by an absorbing reaction with the moisture in the patient's mouth is selected from the group consisting of zeolite, quick lime, silica gel, active alumina, and plaster of Paris.

4. The dental mirror cited in claim 1, wherein the lid is formed to be easily assembled and disassembled with said holding member so that said concave-shaped filling canister can be selectively opened and closed.

5. The dental mirror cited in claim 1, wherein said stem portion and the distal end portion are formed to be detachably assembled and disassembled.

6. A dental mirror for diagnosing and observing a diseased part of a patient's mouth, said dental mirror having a stem portion, a distal end portion, a holding member at the distal end portion, a mirror attached to the holding member, and a receptacle encasing a substance capable of storing heat generated by an absorbing reaction with moisture in the patient's mouth, said receptacle being provided with a plurality of small size through-holes in a first surface thereof, and a sealing film temporarily adhered on said first surface of said receptacle.

7. The dental mirror cited in claim 6, wherein said stem portion and the distal end portion are formed as a unitarily structured component.

8. The dental mirror cited in claim 6, wherein the substance capable of storing heat generated by an absorbing reaction with the moisture in the patient's mouth is selected from the group consisting of zeolite, quick lime, silica gel, active alumina, and plaster of Paris.

9. The dental mirror cited in claim 6, further comprising a lid formed to be easily assembled and disassembled with said holding member so that said holding member can be selectively opened and closed, whereby said receptacle can be encased by said holding member and said closed lid.

10. The dental mirror cited in claim 6, wherein said stem portion and the distal end portion are formed to be detachably assembled and disassembled.

* * * * *